United States Patent [19]

Kifor et al.

[11] Patent Number: 5,658,936
[45] Date of Patent: Aug. 19, 1997

[54] ENHANCEMENT OF ERECTILE FUNCTION WITH RENIN-ANGIOTENSIN SYSTEM INHIBITORS

[75] Inventors: Imre Kifor, Methuen; Gordon Williams, Belmont, both of Mass.

[73] Assignee: Brigham & Women's Hospital, Inc., Boston, Mass.

[21] Appl. No.: 529,486

[22] Filed: Sep. 18, 1995

[51] Int. Cl.$^6$ .......................... A61K 31/41; A61K 31/40
[52] U.S. Cl. ............................................. 514/381; 514/423
[58] Field of Search ................................... 514/381, 423

[56] References Cited

U.S. PATENT DOCUMENTS

| | | | |
|---|---|---|---|
| 5,278,192 | 1/1994 | Fung et al. | 514/645 |
| 5,475,004 | 12/1995 | Heitsch et al. | 514/303 |

OTHER PUBLICATIONS

Trigo-Rocha, F. et al., "The Role Of Cyclic Adenosine Monophosphate, Cyclic Guanosine Monophosphate, Endothelium And Nonadrenergic, Noncholinergic Neurotransmission In Canine Penile Erection", The Journal Of Urology, 1993, 149:872–877.

Kohno, Masakazu et al., "Inhibition By Atrial And Brain Natriuretic Peptides Of Endothelin-1 Secretion After Stimulation With Angiotensin II And Thrombin Of Cultured Human Endothelial Cells", American Society For Clinical Investigation, Inc., 1991, 87:1999–2004.

Ignarro, Louis J., et al. "Nitric Oxide And Cyclic GMP Formation Upon Electrical Field Stimulation Cause Relaxation Of Corpus Cavernosum Smooth Muscle", Biomedical And Biophysical Communcations, 1990, 170:2:843–850.

Harris, Douglas, W., et al., "Stimulation Of Cyclic GMP Formation In Smooth Muscle Cells By Atriopeptin II", Life Sciences, 1985, 37:591–597.

Pickard, R.S., et al., "Evidence Against Vasoactive Intestinal Polypeptide As The Relaxant Neurotransmitter In Human Cavernosal Smooth Muscle", Br. J. Pharmacol., 1993, 108:497–500.

Klinge, E., et al., "Comparative Study of Some Isolated Mammalian Smooth Muscle Effectors of Penile Erection", ACTA, Physiol. Scand, 1977, 100:354–467.

Andersson, K. et al., "Characterization of Immunoreactive Argoimine Vasopressin (AVP) in and Effects of on Isolated Human Penile Erectile Tissues", The Journal Of Urology., 1987, 137:1278–1282.

Croog, S., et al., "Sexual Symptoms in Hypertensive Patients", Arch. Intern. Med., 1988, 148:788–794.

Clark, J., "A Possible Role for Angiotensin II in the Regulation of Male Sexual Behavior in Rats", Physiology And Behavior, 1988, 45:221–246.

Suzuki, H., et al., "Effect of First–Line Antihypertensive Agents on Sexual Function and Sex Hormones", Journal Of Hypertension, 1988, 6(suppl 4):S649–S651.

Walley, T., et al., "Adverse Effects of Captopril in Hospital Outpatients with Hypertension:", Post Grad Med Journal, 1990,66:106–109.

Vickers, M., et al., "Angiotensin Production by Human Corporal Cavernosal Tissue", The Journal Of Urology, 1992, 147:4, No. 100.

Haidle, G., et al, "Guidelines for Drug Treatment of Male Infertility", Drugs, 1:60–68 (1991).

Testa, M., et al., "Quality of Life and Antihypertensive Therapy in Men–A Comparison of Captopril with Enalapril", The New England Journal Of Medicine, 1993, 328:907–913.

Goldstein, I., "Impotence", 62nd Annual Meeting Program Of The New England Section, American Urological Association, Inc—Session II, 1993, pp. 64–65.

Joubert, P., et al., "The Effects of papaverine, Prostaglandin E–1, and Phenylephrine on the Pulsatile Angiotensin II Secretion by Human Corporal Cavernosal Tissue", Journal Of Urology, 1993 149:4:245A, No. 125.

Lopes-Martins, R., "Pharmacological Characterization of Rabbit Corpus Cavernosum Relaxation Mediated by the Tissue Kallikrein–kinin System", Br. J. Pharmacol., 1994, 113:81–86.

Prisant, L.M., et al., "Sexual Dysfunction with Antihypertensive Drugs", Arch Intern Med. 1994, 154:730–736.

Kifor, I., et al., "Tissue Angiotensin II and Impotence", The Endocrine Society 1995 Abstract Form, Jan. 1995.

Andersson, K., et al., "Physiology of Penile Frection", Physiological Reviews, 75:1:191–218 (1995).

Primary Examiner—Kimberly Jordan

[57] ABSTRACT

A method for treating patients having erectile dysfunction is described. The method involves treating patients with a renin-angiotensin system inhibitor. A method for treating a subject to improve erectile function is also described. The method involves treating patients with a renin-angiotensin system inhibitor. Preferably the inhibitor is an angiotensin II antagonist, an ACE inhibitor, or a renin inhibitor.

22 Claims, 4 Drawing Sheets

ENHANCEMENT OF ERECTILE FUNCTION WITH RENIN-ANGIOTENSIN SYSTEM INHIBITORS

BACKGROUND

Erectile dysfunction, or impotence, is a common disorder that occurs in more than 10 million men in the U.S.A. Although psychogenic etiology was thought to be the primary cause of erectile dysfunction, it now is believed that underlying organic diseases are responsible for most instances of erectile dysfunction. This conceptual change is supported by the particularly high incidence of impotence in men with essential hypertension, coronary artery disease and diabetes. In addition, a major mechanism responsible for impotence is an increase in the tone and/or contractility of smooth muscle within the corpus cavemosum penis and penile arteries that impede the modulation of penile blood flow by physiologic regulators. A similar mechanism, an increased tone and/or contractility of vascular smooth muscle, impedes the modulation of blood flow in the coronary, renal, and other arteries of hypertensive, diabetic etc. patients.

Other potential organic causes of erectile dysfunction include endocrine disorders, e.g., testicular failure and hyperprolactinemia; side effects of drugs, e.g., antiandrogens, antihypertensives, anticholinergics, antidepressants, antipsychotics, central nervous system depressants and drugs of habituation or addiction; penile diseases, e.g., Peyronie's disease, previous priapism, and penile trauma; neurological diseases, e.g., anterior temporal lobe lesions, diseases of the spinal cord, loss of sensory input, diseases of nervi erigentes, and diabetic autonomic neuropathy; and vascular diseases, e.g., essential hypertension, aortic occlusion, atherosclerotic occlusion or stenosis of the pudendal artery, venous leak, and diseases of the sinusoid spaces.

Disorders such as essential hypertension, coronary artery disease and diabetes involve an increase in vascular smooth muscle tone which imposes limitations on the modulation of regional blood flow in the kidney, heart, brain and other segments of the vascular bed. Clinical and experimental observations suggest that an imbalance between locally produced Angiotensin II and nitric oxide (NO) leads to an inappropriate tone of vascular smooth muscle resulting in increased blood pressure and altered regional blood flow. Indeed, administrations of nitric oxide synthase (NOS) inhibitors or angiotensin II increase the tone and/or contractility of vascular smooth muscle and systemic blood pressure, thereby decreasing regional blood flow to organs such as the kidney and heart. Conversely, NO, angiotensin II antagonists, renin inhibitors, and angiotensin converting enzyme (ACE) inhibitors decrease the smooth muscle tone and increase regional blood flow to these organs, and decrease systemic blood pressure.

As a modified vascular tissue, ccp produces and secretes the same range of autocrine and paracrine regulators as conventional vascular tissue. The smooth muscle tone of the ccp, however, does not appear to be regulated in the same manner as in the vascular wall. Presently it is postulated that the tone or contractility of ccp is modulated by adrenergic regulation and locally produced NO and endothelin. In the ccp, most studies have been directed to observing the relaxing effects of NO, vasoactive intestinal peptide (VIP), calcitonin gene-related peptide (CGRP) and parasympathetic innervation, which also have similar effects on conventional and ccp vascular smooth muscle.

Although both vascular and ccp smooth muscle are contracted by angiotensin II, this peptide is not considered an important regulator of penile blood flow. In fact, it generally is believed that antihypertensive agents, such as ACE inhibitors and angiotensin II antagonists, can cause sexual dysfunction in male patients. Several studies have been conducted to determine whether antihypertensive agents actually cause erectile dysfunction. The results of the studies were inconsistent. Some studies found that ACE inhibitors caused impotence.

Many male patients with hypertensive diabetes and/or coronary artery disease are impotent. One form of treatment for hypertensive patients, μ blocker administration, exacerbates impotence. Although this patient population is often treated with renin-angiotensin system inhibitors, several studies have concluded that ACE inhibitors, such as captopril, do not show any effect on improving impotence. (Croog et al. *Sexual Symptoms in Hypertensive Patients*, Arch Intern Med 148: 788–794, (1988); Suzuki et al, *Effects of First-line Antihypertensive Agents on Sexual Function and Sex Hormones*, J of Hypertension 6:S649–S651 (1988).

Several therapies have been developed and are currently being used to treat erectile dysfunction. Therapies include treatment with androgens, injection into the corpus cavernosum of smooth muscle relaxing substances such as papaverine, phentolamine, and $PGE_1$, psychotherapy, penile prostheses, and mechanical devices such as those employing a vacuum to cause erection and a restricting means to prevent venous return at the base of the penis. Injection of smooth muscle relaxing substances into the ccp is an efficient method of treatment, successful in 70–95% of cases. The high rate of success indicate that the increased tone of ccp smooth muscle is the most important cause of erectile dysfunction. However, self injection is inconvenient for a large number of patients, it is frequently painful and may cause detrimental side effects such as priapism and penile fibrosis. Penile prostheses are effective but require surgery.

It would be desirable to have a therapy that could be administered systemically and that could avoid the foregoing drawbacks.

SUMMARY OF THE INVENTION

Our studies indicate that similar to the vascular tissue, the corpus cavernosum penis produces and secretes angiotensin II, that plays an important role in modulation of the penile blood flow. Local, intracavernosal, or systemic administration of angiotensin II antagonists or ACE inhibitors has a powerful effect on the penile blood flow. This effect can be used to improve erectile dysfunction without the inconvenience and side effects of drugs used for intracavernosal pharmacotherapy.

The invention relates to a method for treating a subject having symptoms of erectile dysfunction by the administration to the subject of a therapeutically effective dose of a renin-aniotensin system inhibitor to decrease the symptoms of erectile dysfunction. The renin-angiotensin system inhibitor can be selected from the group consisting of an angiotensin II antagonist, an ACE inhibitor, or a renin inhibitor. In one embodiment the angiotensin II antagonist is losartan. A therapeutically effective dose is one which modifies systemic blood pressure by less than 10% within one day of administration. The dose preferably can be low enough whereby systemic blood pressure is lowered within one day of administration by even less than 5%, and in particular so low as to cause no measurable lowering of systemic blood pressure (i.e., no change in systemic blood pressure acutely).

In one embodiment the renin-angiotensin inhibitors of the invention are administered orally. In another embodiment they are administered by intracavernosal injection or penile patches.

Another embodiment of the invention thus pertains to a method for treating a subject to improve erectile function, comprising administering to the subject a therapeutically effective dose of a renin-angiotensin system inhibitor to improve erectile function. Again, the inhibitor can be selected from the group consisting of an angiotensin II antagonist, an ACE inhibitor and/or a renin inhibitor. In one embodiment the angiotensin II antagonist is losartan. A therapeutically effective dose is one which modifies the systemic blood pressure by less than 10%. In one embodiment the renin-angiotensin inhibitors of the invention are administered orally. In another embodiment they are administered by intracavernosal injection or penile patches.

The invention is useful, inter alia, in subjects who are otherwise free of indications for renin-angiotensin system inhibition treatment.

DETAILED DESCRIPTION OF THE DRAWINGS

Figure 8:
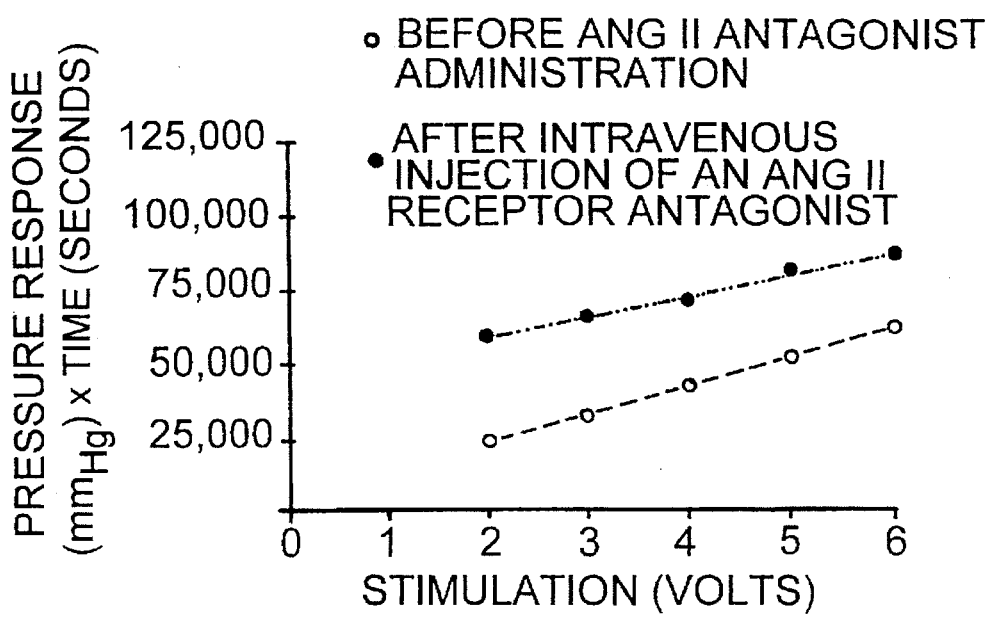

FIG. 8 is a graph which shows the change in intracavenosal pressure in response to stimulation of the pelvic nerve for 10 seconds by various voltages (2–6 V) (the pressure response (mmHg) was multiplied with the duration (in seconds) of high intracavenosal pressure produced by the stimulation of the pelvic nerve and was represented as a function of the intensity of stimulation (voltage)) followed by the administration of an angiotensin II antagonist (losartan) intravenously in a dose equal to or smaller than the dose necessary to reduce systemic blood pressure by 10%.

DETAILED DESCRIPTION OF THE INVENTION

Erectile dysfunction is a disorder involving the failure of a male mammal to achieve erection, ejaculation, or both. Symptoms of erectile dysfunction include an inability to achieve or maintain an erection, ejaculatory failure, premature ejaculation, inability to achieve an orgasm. An increase in erectile dysfunction is often associated with age and is generally caused by a physical disease or as a side-effect of drug treatment.

Surprisingly, it has been discovered that treatment of subjects with antihypertensive agents, in particular with a renin-angiotensin system inhibitor, reduces symptoms of erectile dysfunction in subjects having erectile dysfunction or increases erectile function in normal subjects. It was unexpected that inhibitors of the renin-angiotensin system would be effective in reducing symptoms of erectile dysfunction as well as improving erectile function at a dose which does not reduce the systemic blood pressure by more than 10%. Inhibitors of the renin-angiotensin system are antihypertensive agents, and therefore are generally believed to either have no effect or a negative effect on erectile dysfunction.

In one embodiment, the present invention relates to a method for treating a subject having symptoms of erectile dysfunction by administering to a subject a therapeutically effective dose of a renin-angiotensin system inhibitor to decrease the symptoms of erectile dysfunction. The renin-angiotensin inhibitor can be, for example, an angiotensin II antagonist, an ACE inhibitor, or a renin inhibitor. The renin-angiotensin system inhibitor can be administered in an effective dose which does not reduce the systemic blood pressure within one day of administration by more than 10%. Acute lowering of systemic blood pressure by 10% or more is believed to cause sexual dysfunction, the opposite of the desired goal of the invention. It is preferred that the dose be low enough to cause an acute lowering of systemic blood pressure by no more than 5%. In one embodiment, the therapeutically effective dose is sufficient to increase intracavernosal pressure to a level substantially the same as the mean arterial pressure.

The term "subject" as used herein, is intended to mean humans, primates, horses, cows, swine, goats, sheep, dogs, and cats.

In one embodiment, the subjects treated by the methods of the present invention are otherwise free of indications for renin-angiotensin system inhibition treatment. By "free of indications for renin-angiotensin system inhibition treatment", it is meant that the subject does not have indications (e.g., symptoms or a clinical history) which, prior to the present invention, were known to involve treatment with a renin-angiotensin system inhibitor. For example, it previously has been shown that renin-angiotensin system inhibitors can be used to treat hypertension, congestive heart failure, myocardial infarction and renal disease.

The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1–8] octapeptide). The latter is an active pressor substance which has been implicated as a causative agent in several forms of hypertension in various mammalian species, e.g., humans.

Renin-angiotensin system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin -(1–8) octapeptide and related analogs); N-substituted imidazole-2-one (U.S. Pat. No. 5,087,634); imidazole acetate derivatives including 2-N-butyl-4-chloro-1-(2-chlorobenzile)imidazole-5-acetic acid (see Long et al., *J. Pharmaeol. Exp. Ther.* 247(1), 1–7 (1988)); 4, 5, 6, 7-tetrahydro-1H-imidazo[4, 5-c]pyridine-6-carboxylic acid and analog derivatives (U.S. Pat. No. 4,816,463); N2-tetrazole beta-glucuronide analogs (U.S. Pat. No. 5,085, 992); substituted pyrroles, pyrazoles, and tryazoles (U.S. Pat. No. 5,081,127); phenol and heterocyclic derivatives such as 1,3-imidazoles (U.S. Pat. No. 5,073,566); imidazofused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35,45)-4-amino-3-hydroxy-5-cyclohexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, Pennsylvania); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G. D. Searle and Company).

Angiotensin converting enzyme, or ACE, is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075, 451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063, 207, 5,036,054, 5,036,053, 5,034,512, and 4,894,437).

Preferably the renin-angiotensin system inhibitor is administered in a therapeutically effective dosage. A therapeutically effective dose is one that is sufficient to achieve improvement in erectile function or an alleviation of the symptoms of erectile dysfunction.

Effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation.

Generally, systemic doses of active compounds will be from about 0.01 milligrams/kg body weight per day to 10 milligrams/kg body weight per day. It is expected that oral doses in the range of 0.1 to 100 milligrams/kg body weight, in one or several administrations per day, will yield the desired results. In the event that the response in a subject is insufficient at such doses, even higher doses (or effective higher doses by a different, more localized delivery route) may be employed to the extent that patient tolerance permits. In the event that lower doses are sufficient to improve erectile function lower doses may be employed. Multiple doses per day are contemplated to achieve appropriate systemic levels of compounds. In one embodiment a maximal dose is administered first, followed by submaximal dosages. A therapeutically effective dose is less than that which will have the effect of acutely modifying the systemic blood pressure greater than 10%. It preferably is so low so as to acutely modify systemic blood pressure by no more than 5% and can be even so low so as to have no measurable acute effect on systemic blood pressure. In one embodiment a therapeutically effective dose of a renin-angiotensin system inhibitor is sufficient to increase the intracavernosal pressure to a level substantially the same as the mean arterial pressure.

In an alternate embodiment, the invention provides a method for treating a subject to improve erectile function by administering to the subject a therapeutically effective dose of a renin-angiotensin system inhibitor to improve erectile function. The subject in this embodiment is not necessarily exhibiting symptoms of erectile dysfunction. An improvement in erectile function is defined herein as any enhancement in the ability of a subject to maintain an erection, induce or improve ejaculation, induce or improve orgasm, and increase libido.

A variety of administration routes are available. The particular mode selected will depend of course, upon the particular drug selected, the severity of the erectile dysfunction being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, intracavernosal injection and parenteral routes. The term "parenteral" includes subcutaneous, intramuscular, and the like. Oral administration will be preferred because of the convenience to the patient as well as the dosing schedule.

The compositions containing the renin-angiotensin inhibitor conveniently may be presented in unit dosage form and may be prepared by any of the methods well known in the art of pharmacy. Such methods include the step of bringing the active ingredient into association with a carrier which constitutes one or more accessory ingredients. In general, the compositions are prepared by uniformly and intimately bringing the renin-angiotensin inhibitor into association with a liquid carrier, a finely divided solid carrier, or both, and then, if necessary, shaping the product.

Injectable compositions and oral preparations are particularly contemplated. Suitable formulations may be found in Remington's Pharmaceutical Sciences. Preferred compositions suitable for parenteral administration conveniently comprise a sterile aqueous preparation of the renin-angiotensin inhibitor. This aqueous preparation may be formulated according to known methods using those suitable disbursing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono or di-glycerides. In addition, fatty acids such as oleic acid find use in the preparation of injectables.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion. Oral formulations of renin-angiotensin system inhibitors are well known.

EXAMPLES

Example 1

Angiotensin II is produced and secreted by the ccp

METHODS:

Tissue preparation. Human tissue consisting of 100–200 mg ccp devoid of conduit vessels was obtained from 22 patients undergoing penile prosthesis implantation. Dog and rat ccp tissue samples were obtained from 3 anesthetized dogs and 6 rats. The tissues were used for four procedures: 1) Angiotensin content (four human samples immediately frozen in liquid nitrogen and kept at −70° C. until analysis); 2) Immunohistochemistry (two human, three dog and six rat samples assigned for immunohistochemistry were embedded in embedding medium (O.C.T. compound, Miles Inc. Elkhart, Ind.) and quick frozen in small vials containing isopentan cooled with liquid nitrogen or dry ice); 3) Superfusion (twelve human samples placed immediately into ice cold culture medium DMEM containing an additional amount of 0.1% protease free bovine serum albumin (BSA) (Boehringer Mannheim Corp. Indianapolis, Ind.); and 4) Single cell studies (four human samples prepared as noted under 3)).

1) Angiotensin content

Small pieces, about 15–35 mg of frozen tissue were weighed, homogenized in a cooled glass-Teflon homogenizer in 100 microliters of 8M urea containing 0.1% Triton×100, suspended in 2 ml of 80% methanol, 10 mM sodium acetate and 0.5% trifluoroacetic acid, and centrifuged at 13,000 g for 10 minutes. The supernatant was transferred to a polethylene tube containing 50 microliters of 10% glycerol. The pellet was resuspended twice with 2 ml of solvent, dispersed by sonication, and centrifuged. The supernatants were pooled, and the solvent evaporated in a vacuum concentrator. The residue, dissolved in glycerol, was stored at −20° C.

The angiotensin peptides in the tissue extracts were separated as previously described[1]. Briefly, the dried residue was dissolved in 1.2 ml ice cold saline and centrifuged at 13,000 g for 10 minutes. One ml of supernatant was used for peptide separation. An LKB Gti all titanium HPLC system and a Merck 12.5 cm LiChroCart cartridge column with a 4 mm pre-column cartridge filled with 3 micron particles were used. A non-linear gradient of methanol and water, buffered with triethylamine and phosphoric acid was used as described previously[1].

Radioimmunoassay was used to determine the angiotensin content of HPLC fractions and superfusates A double antibody method was used as previously described. The first antibodies, a rabbit anti Ang 1, and a rabbit anti Ang II antibody cross-reacted 100% with the corresponding des-asp angiotensins, i.e. the peptides 2–10 and 2–8 and in a lesser degree with other angiotensin peptide fragments. This cross-reactivity made it possible to identify angiotensin peptides separated by HPLC. However, the cross-reactivity did not interfere with the quantitation of individual peptides by RIA after HPLC.

2) Immunohistochemistry

About 4–10 micron frozen sections were air dried for 5 minutes and fixed with cold (−20° C.) acetone for 10 minutes. The endogenous peroxidase was blocked using Dako peroxidase blocking reagent (Dako Corporation, Carpinteria, Calif.), and non-specific protein binding was suppressed by exposing the slices to Dako blocking solution for an hour. After washing, the slices were incubated for an hour with the first antibody, and after repeated washing with Dako washing solution the slices were incubated with the peroxidase labeled second antibody (Dako). Finally, after washing, the slices were incubated with a Dako AEC substrate system for 15 minutes, washed and mounted using mounting solution. Adjacent slices were used as controls. The controls were incubated with pre-immune serum of the same species as the first antibody, or the anti Ang II antibody was saturated with synthetic Ang II prior to application.

3) Superfusion

Ang II secretion by superfused human ccp tissue slices was measured as previously described for adrenal tissue[2]. Briefly, about 80–100 mg human ccp tissue kept in refrigerated DMEM was chopped to ≦1 mm diameter pieces on an ice cool platform. Then the whole mass was transferred to an electronic analytical balance atop of several layers of filter paper, and two to three equal aliquots, weighing 15–30 mgs. were quickly removed, mixed with preswollen Sephadex G 10 beads and loaded in parallel superfusion chambers. The superfusion system of Forma Scientific was used (Forma Scientific, Marietta, Ohio). Medium 199 (GIBCO, Grand Island, New York, N.Y.) buffered with 25 mM sodium bicarbonate, aerated with a mixture of air and 5% $CO_2$ was used for superfusion. The medium contained 0.1% tissue culture grade BSA, and had a potassium concentration of 3.7 mM. The flow rate was 0.2 ml/min/chamber. The superfusate was collected in 15 minute periods using a cooled (0° C.) fraction collector. The collected fractions were quick frozen in a dry ice-ethanol mixture and then lyophilized and kept at −20° C. until use. After reconstitution the Ang II content of the fractions was determined by RIA. Twelve tissue samples were superfused for 210 minutes and without additional stimulation or inhibition Ang II secretion. Six tissue samples were superfused in three parallel chambers. One chamber served as a control, two additional chambers were superfused for 60 minutes as the control, then one chamber was superfused for an additional 120 minutes with medium 199 containing 20 micromolar papaverine and the other chamber with medium containing 8.5 nanomolar PGE.

RESULTS:

The angiotensin peptide content of the human corpus cavernosum.

The peptides in human ccp extracts were separated by HPLC. Several angiotensin peptides, such as 1-10, 1-8, 2-10, 2-8, 1-9, 1-7, 1-6, 1-5, 5-8, were identified by with synthetic fragments and reaction with an antibody. Four peptides: Ang I, Ang II, des-asp-Ang I, and des-asp-Ang II were found to represent more than 90% of angiotensin peptides within the human ccp and were quantitated by RIA (Table I). While the Ang II content of the human ccp was 1178 femtomol/g tissue, the plasma Ang II concentration on a normal sodium diet, determined using a similar technique, was 6.3±3.4 femtomol/ml (n =12). Thus, the ccp Ang II content was almost 200-fold higher than the Ang II concentration in a comparable volume of normal plasma. The Ang I content of the ccp was also much higher than the plasma level. The Ang II concentration in the ccp was much higher than in aorta (85 pg Ang II/g tissue) or in mesenteric artery (184 pg/g tissue)(45), suggesting that the ccp is a high Ang II-producing tissue. The concentration of des-asp angiotensins, degradation products of Ang I and Ang II, though somewhat different than their precursor peptides, were still in a similar range as Ang I and Ang II.

TABLE 1

Angiotensin peptide content of human ccp

| Peptide | fmol peptide/gram tissue ± SEM (n = 74) |
| --- | --- |
| Angiotensin I | 528 ± 171 |
| Des-asp-Ang I | 475 ± 67 |
| Angiotensin II | 11178 ± 223 |

The distribution pattern of Ang II within the corpus cavernosum penis.

Many cells and cell clusters within the human tissue samples showed a strong positive reaction for Ang II. However, the small size of specimens limited our ability to determine the distribution pattern of Ang II containing cells within the human ccp. The animal models were a much better source of information. Longitudinal and cross sections through the rat ccp and cross sections from dog ccp indicated that Ang II has a non-uniform distribution pattern with several cell types containing Ang II identified in the ccp (data not shown). The endothelial cell layer lining the arteries and the cavernosal cavities displayed a strong positive reaction for Ang II, suggesting that most endothelial cells contained Ang II. The smooth muscle layer of arteries embedded in ccp also displayed a uniform positive reaction indicating that they also contain Ang II. However, the staining of ccp smooth muscle was inconsistent. A strong, positive reaction was observed in unidentified cell clusters within the smooth muscle, but in general the smooth muscle displayed a weak histochemical reaction. It is estimated that about 5–10% of the visible cells within the ccp smooth muscle layer displayed a strong immunochemical reaction. In the absence of the anti-Ang II antibody no color reaction was produced. Therefore, the ccp has several cell types producing Ang II.

Ang II secretion by superfused non-stimulated human ccp slices.

Figure 1:
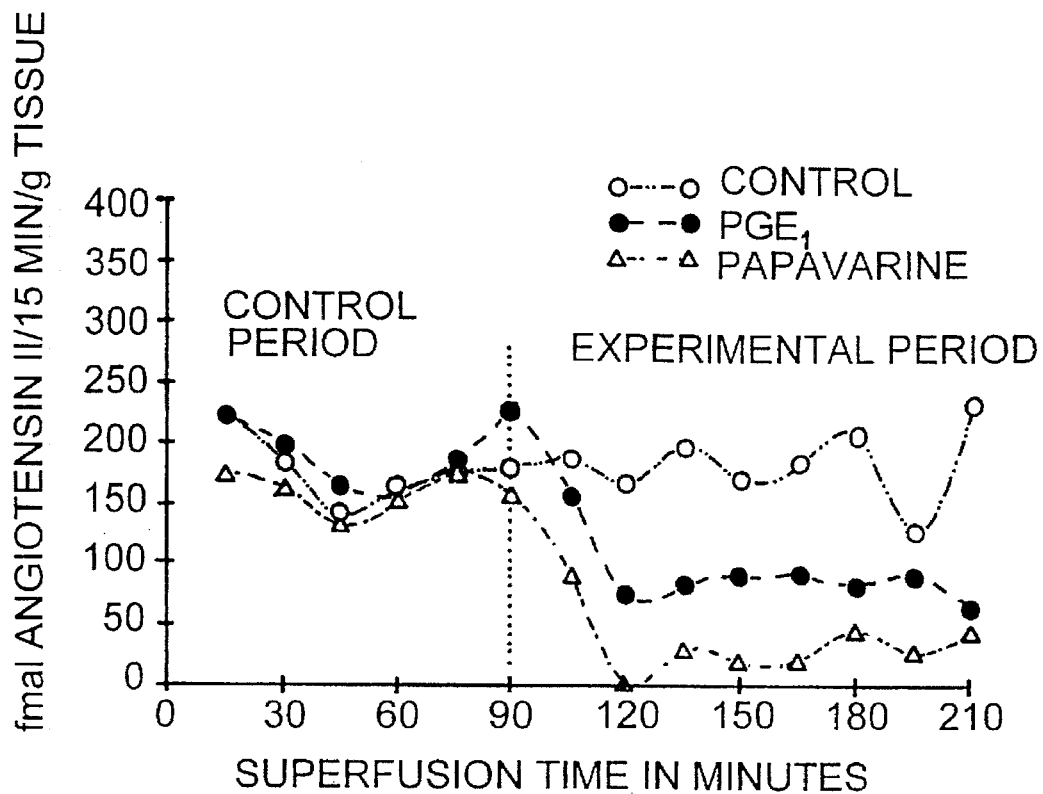
FIG. 1 is a graph which shows that superfused human corpus cavernosum penis tissue slices (10–20 mg each) continuously secrete Ang II in an oscillatory pattern and that addition of papaverine in 20 micromolar or PGE, in 8.5 nanomolar concentration to the superfusion medium suppressed quickly Ang II secretion.

Superfused human ccp tissue releases immunoreactive Ang II (Ang IIir) into the medium in a sustained, somewhat oscillatory pattern over the course of 3 hours (FIG. 1). An Ang IIir secretion rate of 57±11 femtomol/g tissue/minute was calculated with a range of 4–137 fmol/g tissue/min (n=12). Similar to the adrenal zona glomerulosa, local Ang II production is able to contributes more to the extracellular levels of Ang II than the plasma levels. The high rate of unstimulated Ang IIir secretion would be enough to drain the mean tissue Ang II content in roughly 20 minutes, indicating that most of the Ang II released in the 3-hour period must be produced within the tissue. Adrenal glomerulosa cells exhibit a similar phenomenon[2]. The effective Ang II concentration within the extracellular space of the ccp also depends on the rate of peptide degradation by non-specific, external peptidases[3]. If this activity is high in the ccp, our results obtained using tissue slices will be an underestimation Ang II secretion. The degradation products des-asp-Ang I and des-asp-ANG II are contained in a different intracellular pool that is not secreted, therefore the des-asp angiotensins will not contribute significantly to Ang IIir. Due to extracellular peptidase activity superfused tissue slices could appear to "release" some angiotensin peptide fragments, which are produced by these cell surface enzymes. Therefore we use the terms, immunoreactive Ang I or Ang II (Ang Iir, Ang IIir), when RIA is not preceded by HPLC.

Angiotensin secretion by enzymatically-dispersed cells of human corpus cavernosum A small (<10%) portion of the ccp cell population displayed a blue halo around the cells in the presence of anti-Ang II antibody indicating Ang II secretion (data not shown). While these secretory ccp cells have not yet been identified, based on the immunohistochemistry studies described above these secretory cells are most likely vascular and ccp endothelial cells, the intima of penile arteries and/or specialized cells within the smooth muscle compartment of ccp. The size distribution patterns differed between non-secretory and secretory cells. The non-secretory cells showed a single major peak, while the secretory cells showed a multimodal distribution. The distribution pattern is due to a substantial subpopulation of secretory cells which was found to be considerably larger than the rest of the secretory and non-secretory cells (data not shown). These cells had an area of 80–110 micron$^2$ and comprised approximately 20–30% of the secretory cells.

Figure 2:
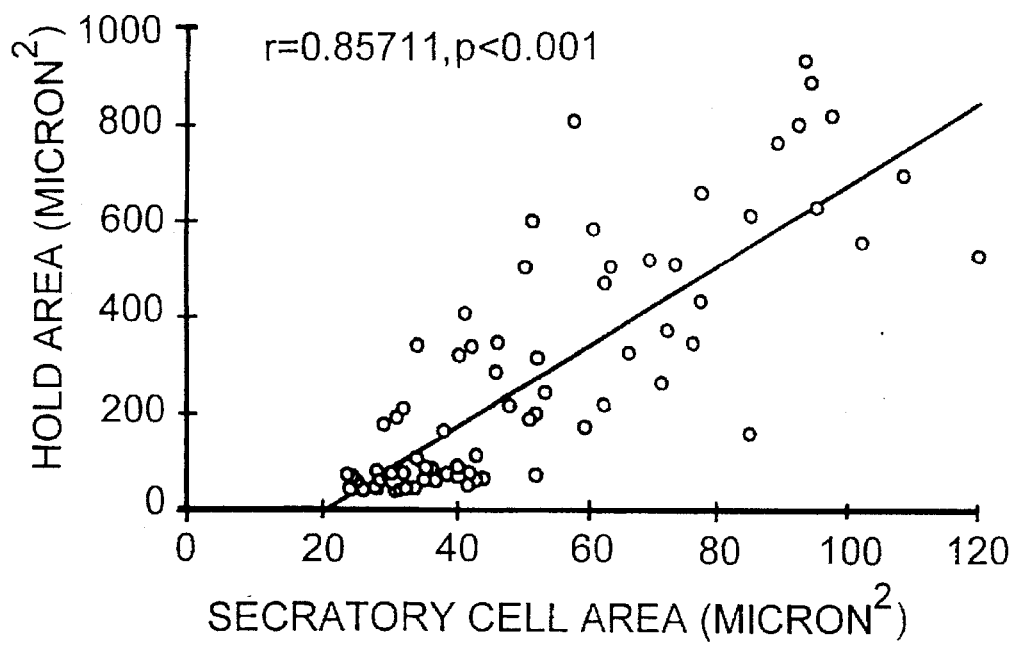
FIG. 2 is a graph which shows that there is a significant correlation between the size (area) of secretory cells and the area of the halo produced by secretory cells.

A significant correlation between the size (area) of Ang II secreting cells and the area of halos produced around secretory cells was observed (FIG. 2). A similar significant correlation (r=0.85203, p<0.001) was established between the size (area) of Ang II secreting cells and the area IGV, the integrated gray value of the pixels within the area boundary, and the area of secretory cells and the intensity of the spots. These relationships indicate that larger cells produce larger and darker halos, i.e. secrete more Ang II.

Example 2

Smooth muscle relaxing drugs partially inhibit secretion of Angiotensin II from ccp

METHODS:

Single cell studies

The enzymatic dispersion of tissue samples into single cells was performed as previously described[4]. Briefly, about 50 mgs human ccp tissue assigned for single cell production by enzymatic dispersion was chopped in small pieces ≦1 mm on an ice cool support, transferred in 1 ml DMEM medium containing 1 mg/ml collagenase/dispase with low trypsin-like activity, 0.5 mg/ml DNASE (Boehringer-Mannheim Corp. Indianapolis, Ind.), 0.01% BSA, and 200 mg glucose/100 mls and incubated for 60 minutes at 37° C. The media was buffered with 25 mmol sodium bicarbonate and 5% $CO_2$. The collagenase with a low trypsin-like activity was previously selected for high yield of functionally intact cells, responsive to stimulation or suppression. The dispersion was facilitated by pipetting the tissue slurry 20 times after 30 and 60 minutes of incubation using a wide tip polyethylene pipette. After 60 minutes incubation and dispersion the cell suspension was filtered through a 30 micron nylon mesh. The dispersed cells were washed twice with 2 mls DMEM, resuspended in DMEM containing 0.025% BSA and incubated for 30 minutes at 37° C.

Immuno cell blot assay for Ang II.

The immunocell blot assay was performed as previously described[4]. Briefly, multiple aliquots of 20 μls cell suspension, containing about 200 cells, were incubated on Millipore Immobilon-P hydrophobic transfer membrane (Multiscreen-IP in 96 well microliter plate format) for 30 minutes, at 37° C., supplied with water saturated air, containing 5% $CO_2$. After 30 minutes preincubation for sedimentation and cell attachment, test substances dissolved in 2 microliters of DMEM were added to the droplets, and the incubation continued for an additional 60 minutes. Ang II binds to the transfer membrane around the secretory cells. This membrane bound Ang II is detected and visualized by coupling an anti-Ang II antibody and an alkaline phosphatase or peroxidase labeled second antibody with exposure to a proper substrate. The biotinylated second antibody and the avidin coupled peroxidase or alkaline phosphatase are available as kits (Vector Labs, Burlingame, Calif., or Dako Corporation, Carpinteria Calif.). The substrates are also available as kits (Vector Labs, Burlingame Calif., or Dako Corporation, Carpinteria Calif.). Ang II secreting cells appear as dark spots (secretory cells) surrounded by a colored halo. The color is substrate dependent. The size (area) of secretory cells and halos, and the intensity of the spots are determined using video image analysis equipment as described[4].

RESULTS:

The effect of papaverine and PGE on Ang II secretion by superfused ccp tissue.

Figure 3:
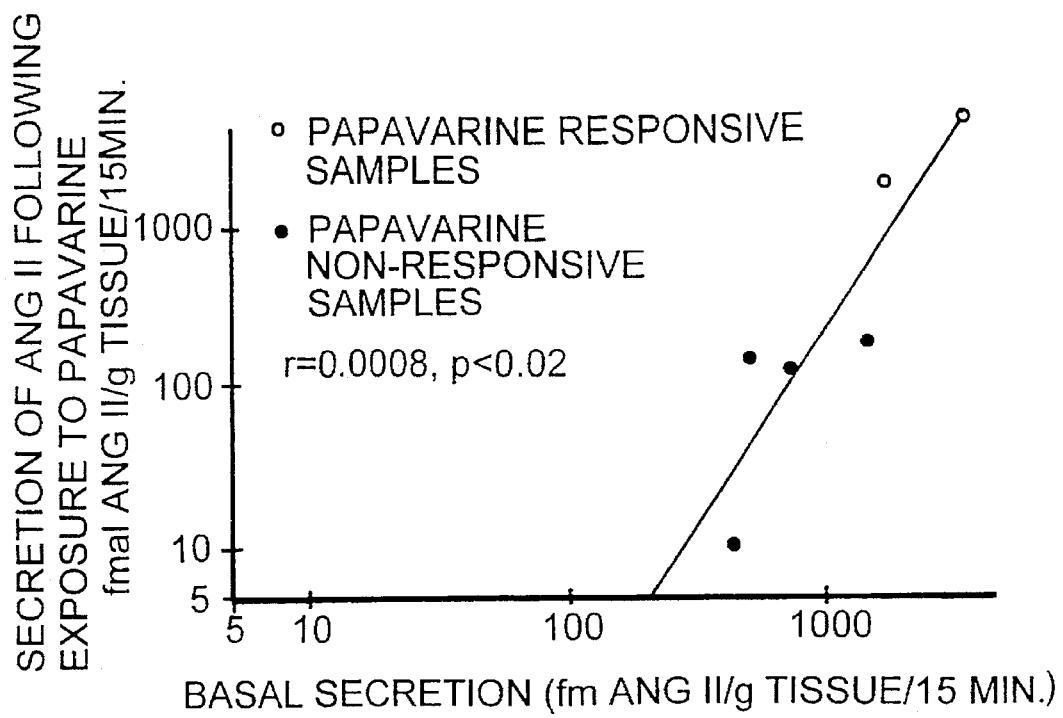
FIG. 3 is a graph which depicts the responsiveness of Angiotensin II secretion to suppression by papaverine.

The effects of papaverine and $PGE_1$ on Ang II secretion were studied in the human ccp. Equal amounts of the same human tissue sample were superfused in three parallel chambers (n=6). Addition of papaverine sharply suppressed the Ang IIr secretion in 4 out of 6 samples, while in 2 samples the Ang II secretion did not change. $PGE_1$ suppressed Ang IIr secretion in 5 out of 6 experiments. The time course of the effect of papaverine and $PGE_1$ on Ang IIir secretion in responsive tissue is shown in FIG. 1. Both papaverine and $PGE_1$ reduced Ang II secretion by responsive superfused tissue slices by about 80% in the first 20 minutes of exposure to these drugs. When cumulative values were compared, papaverine reduced the unstimulated Ang II secretion by 86% in the first hour and 73% in the second hour of superfusion, while $PGE_1$ reduced Ang II secretion by 67% and 43%, respectively. The inhibitory effect of papaverine and $PGE_1$ appeared to be a function of the unstimulated levels of Ang IIir secretion. There was a significant (r=0.9754, p<0.001) correlation between the logarithm of the unstimulated Ang II secretion and the logarithm of papaverine-suppressed Ang II secretion in the same sample (FIG. 3). A similar trend was observed between the logarithm of the unstimulated Ang II secretion and the logarithm of the $PGE_1$-inhibited Ang II secretion (r=0.7938). Thus, the tissues with the highest rates of Ang IIir secretion were only weakly, if at all, responsive to papaverine or $PGE_1$.

The effect of papaverine and $PGE_1$ on Ang II secretion by enzymatically dispersed single cells.

Figure 4:
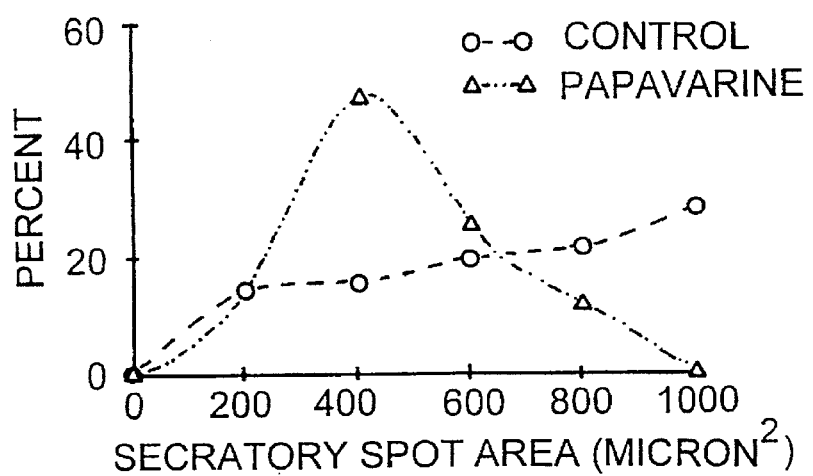
FIG. 4 is a graph which shows that papaverine reduced the area of secretory halos around secretory cells and shifted the distribution curve to the left, which could indicate large oscillations in Ang II release.
Figure 5:
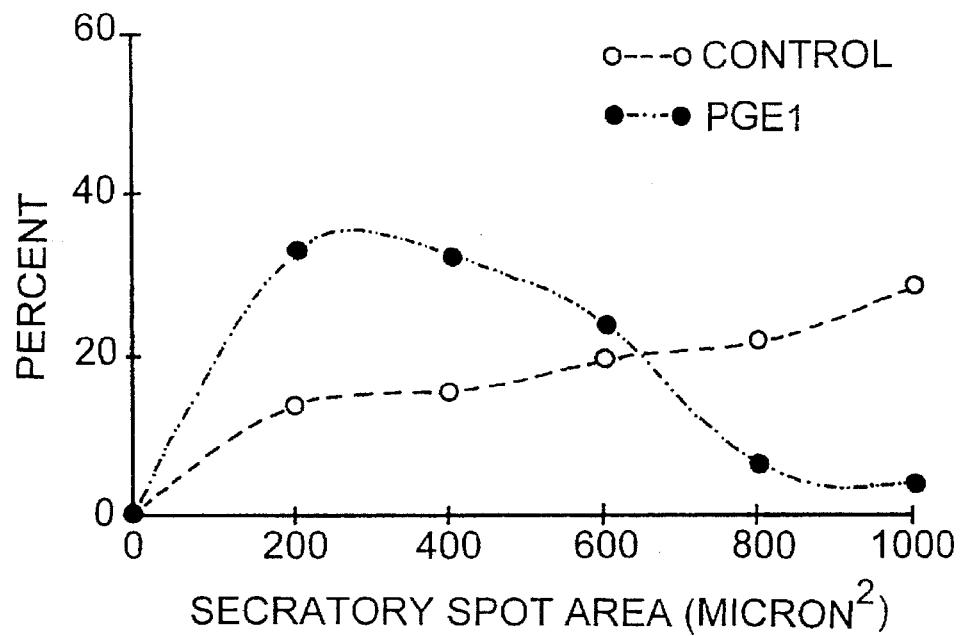
FIG. 5 is a graph which shows that $PGE_1$ had a similar effect on angiotensin II secretion to that of papaverine shown in FIG. 4.

The Immuno-cell blot assay was used to assess the effect of ccp modulators on Ang II secretion for single ccp cells. For this purpose, four 20 μl aliquots of a ccp cell suspension (100–200 secretory cells/20 μl) were incubated with each drug for 60 minutes. The area of the spots generated around secretory cells was measured and the frequency distribution of spot sizes was determined. In the control group nearly 20% of the total secretory spot area was produced by very large spots with an area >1000 μm$^2$, 50% was produced by spots with an area of 400–1000 μm$^2$, and 30% was produced by spots with an area <400$^2$ μm. Papaverine and $PGE_1$ shifted the size distribution curves to the left, toward smaller spots and a smaller cumulative spot area. In $PGE_1$ and papaverine-treated groups, 65% and 60% of the secretory spot area was produced in secretory spots smaller than 400 μm$^2$ and spot areas >1000$^2$ μm were noticeably absent (FIG. 4 and FIG. 5).

The integrated gray value of the pixels within the area boundary of spots (IGV), a measure of spot area x spot intensity, showed similar results. Thus the smaller mean secretory spot area and smaller mean area IGV reflect important changes in the distribution pattern of secretion. The parameters measured by the immuno-cell blot assay are cumulative values and a shift in the distribution pattern of secretory spot areas or IGV's likely reflects major changes in the dynamics of the secretory process (FIG. 4 and FIG. 5).

Example 3

Angiotensin II plays a role in the modulation of ccp smooth muscle tone

METHODS:

In vivo studies

Male dogs of 50–75 lbs were pre-medicated with intramuscular acepromazine (0.5–1 mg/kg) and 0.04 mg/kg atropine. After i.v. administration of pentothal (25 mg/kg), anesthesia was maintained with a pentothal drip. The animals were supported with intravenous lactated Ringer's solution. Blood pressure and heart rate were monitored. The corpora cavernosa were exposed through a skin incision on the ventral surface of the penis. Butterfly needles (19 G) were inserted into each corporal body and were connected to pressure transducers and transducer amplifiers (Gould) allowing injection of drugs or vehicles into the ccp, and to monitoring of intracavernosal pressure. Since the cavernosal bodies usually do not communicate in dogs, the intracavernosal pressure can be very different in the parallel bodies. We used one body for pharmacologic studies while the contralateral body was used as a non-medicated control. The femoral artery was also exposed and cannulated to monitor systemic blood pressure.

RESULTS:

The effect of intracavernosal injection of Ang II into the ccp of anesthetized dogs.

Anesthesia causes an erection in some dogs. The intracavernosal pressure which is pulsatile and high, is close to the mean arterial pressure. Intracavernosal injection of Ang II (0.025 mg) decreased intracavernosal pressure in seconds. The overflow of Ang II into the systemic blood flow caused a short term increase of systemic blood pressure. Intracavernosal administration of epinephrine elicited a similar effect as Ang II, while injection of the same volume of saline had no effect on the intracavernosal pressure.

The effect of a non-peptide Ang II receptor blocker losartan on intracavernosal pressure.

Figure 6:
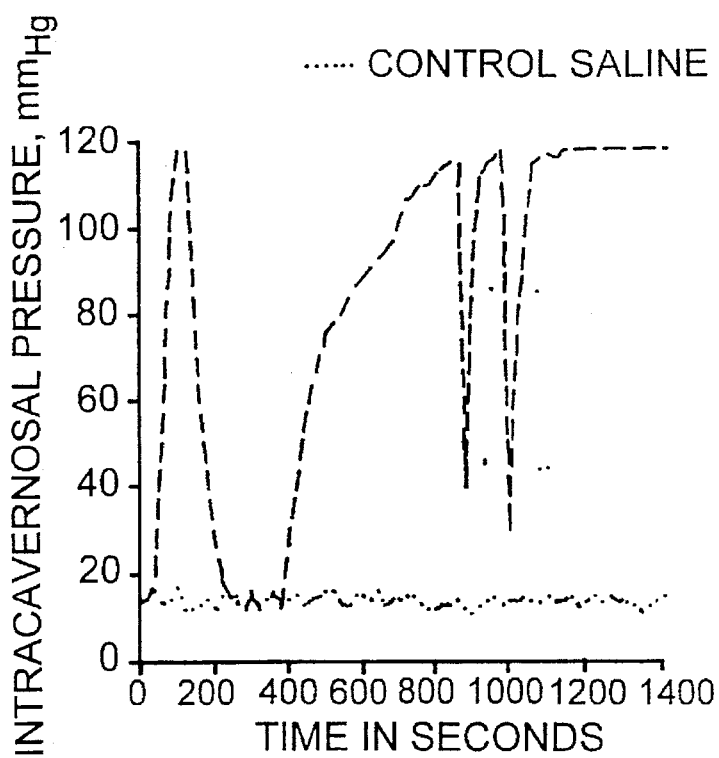
FIG. 6 is a graph which shows that slow intracavenosal injection of an angiotensin II antagonist, losartan, in a dose of 1 mg/kg body weight causes erection in anesthetized dogs lasting 20–40 minutes.

Injection of losartan into one corpus cavernosum of the anesthetized dogs caused a dose dependent (FIG. 6), and biphasic increase in intracavernosal pressure compared with the non-medicated corporal body of the same dog. A dose of 1 mg losartan/kg weight (30–40 mg/dog) increased intracavernosal pressure to the level of arterial pressure for more than 40 minutes (FIG. 6). 1 mg losartan/kg body weight decreases systemic blood pressure in dogs by 10%. A fraction of this dose, i.e. 4–8 mg/dog causes an initial erection, followed by multiple waves of increased intracavernosal pressure with a decreasing amplitude and duration.

The effect of losartan was clearly cumulative. A second injection of 1 mg/kg weight of losartan shortly after the termination of "erection" caused by the first injection caused a much larger and longer lasting increase in intracavernosal pressure. Overall, the intracavernosal pressure becomes less stable after losartan injection.

This observation was further supported in an experiment in which intracavernosal injection of 1.5 ml saline in the non-medicated control cavernosal body of anesthetized dog causes a sharp, short lasting (several seconds) increase in cavernosal pressure. A saline bolus (1.5 ml) applied after a small dose of losartan (1–8 mg/dog) produced a dramatic increase in the peak cavernosal pressure and a prolonged decay curve, suggesting that the ccp was still relaxed. The magnitude of this pressure change (pressure change x time) is well-correlated with the dose of losartan previously injected and with the elapsed time.

Figure 7:
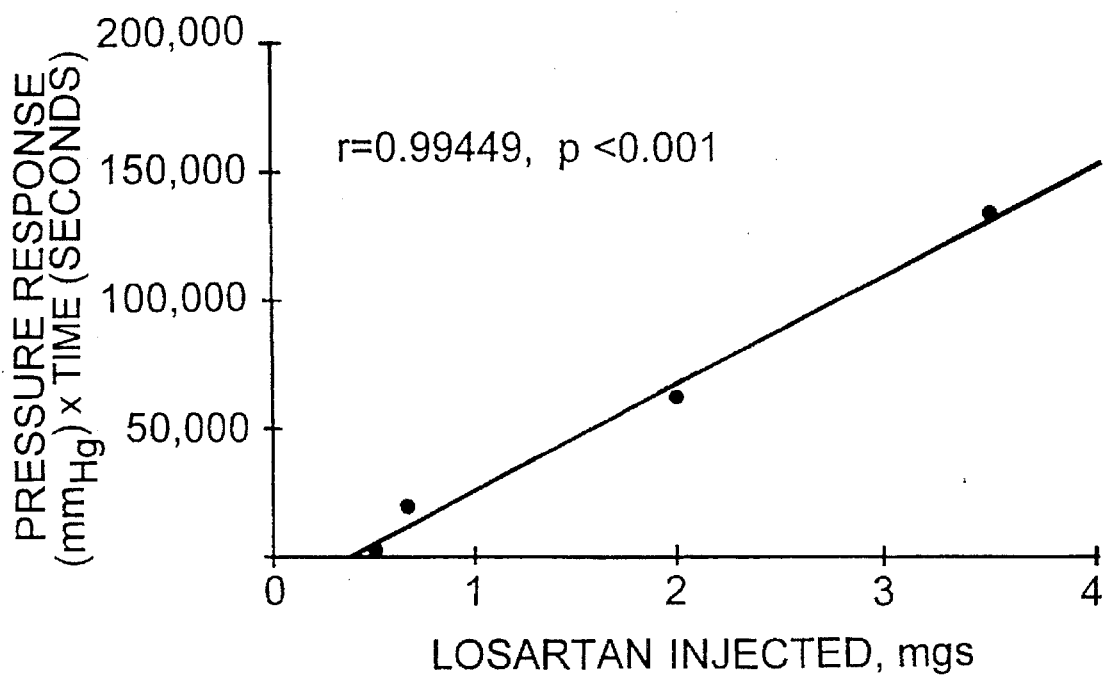
FIG. 7 is a dose response curve which shows that the change in pressure to intracavenosal injection of the angiotensin II receptor antagonist losartan was dose dependent.

The effect of losartan is dose dependent if the small doses are injected in appropriate time intervals, of about 30 minute periods (FIG. 7). We used a fraction of that losartan dose (4–8 mg/dog) and observed an increased intracavernosal pressure up to mean arterial pressure. The duration of the high intracavernosal pressure was a function of losartan dose.

With a dose of 8 mg/dog or larger, losartan produces a long-lasting (20–40 minute) erection. Conversely, control injection of the same volume of saline (1.5 ml) into the non-medicated contralateral chamber of ccp causes a small, transient increase (several seconds) in intracavernosal pressure. With an intermediate dose of 8–16 mg/dog, erections lasted longer than 15–20 minutes, with repeated injection of saline during the post-erection period still caused a larger peak area and slower recovery. The peak area eventually decreased over time and became similar to the control value. This observation suggests that the smooth muscle tone within the ccp decreased not only during the period of erection, but also during the post-erection period. This phenomenon allows a determination of the half-life of the losartan effect under in vivo conditions to be made. The constantly monitored systemic blood pressure did not show changes in systolic or diastolic pressure during these experiments.

Bilateral stimulation of the pelvic nerves causes a transient, 1–2 min increase in cavernosal pressure that is related to the duration of stimulation. Following injection of losartan, intracavernosal pressure and duration significantly increased in a dose-dependent manner, while pressure in the cavernosal chamber that was not exposed to losartan increased only briefly and to a lesser extent. This result suggests that blocking of AngII receptors can facilitate the actions of physiological smooth muscle relaxing regulators and may increase the sensitivity of the ccp.

Example 4

Systemic administration of a renin-angiotensin system inhibitor is effective in increasing blood flow and intracavernosal pressure in ccp The effect of intravenous injection of Ang II receptor antagonist on penile blood flow and intracavernosal pressure in response to pelvic nerve stimulation.

We stimulated the pelvic nerve of the anesthetized dog with increasing voltages within the range of 1–10 V for 10 seconds and measured the reactive blood flow increase in the ccp and the intracavernosal pressure change during this control period. There was a significant linear correlation between the voltage used to stimulate the pelvic nerve and the extent and duration of intracavernosal pressure elicited by the stimulation of pelvic nerve. We then injected intravenously a non-peptide Ang II receptor antagonist at one of three doses. (1 mg/kg body weight, 0.3 mg kg body weight, and 0.1 mg/kg body weight. The dose of 1 mg drug/kg body weight reduces the systemic blood pressure by 10%, the smaller doses have no significant effect on the systemic blood pressure). The highest dose of the Ang II receptor antagonist caused a marginal (<10%) decrease in systemic blood pressure but increased unstimulated blood flow in ccp. The stimulation of pelvic nerve caused a significantly larger increase in pelvic blood flow and intracavernosal pressure than the same level of stimulation performed during the control period (FIG. 8). This suggests that systemic administration of Ang II receptor antagonists could be used to improve the regional blood flow in the ccp. None of the currently employed drugs used in the treatment of impotence can be applied systemically to increase penile blood Each of the foregoing patents, patent applications and references is incorporated by reference in its entirety herein by reference. It should be understood that various changes and modification of the embodiment described above may be made within the scope of this invention. Thus, it is intended that all matter contained in the above description shall be interpreted in an illustrative and not limiting sense.

REFERENCES

1) Kifor I., Moore T. J., Fallo F., Sperling E., Menachery A., Chiou C.-Y., Williams G. H., The effect of sodium intake on angiotensin content of the rat adrenal gland. Endocrinology 1991; 128: 1277–1284.

2) Kifor L., Moore T. J., Fallo F., Sperling E., Chiou C.-Y., Menachery A., Williams G. H., Potassium stimulated angiotensin release from superfused adrenal capsules and enzymatically dispersed cells of the zona glomerulosa. Endocrinology 1991; 129:823–831.

3) Bauer K., Degradation and biological inactivation of thyrotropin-releasing hormone and other neuropeptides. In: Integrative Neuroendocrinology: Molecular, Cellular and Clinical Aspects. McCann, Weiner, eds. Basel, Karger 1987, p. 102–114.

4) Chiou C.-Y., Williams G. H., Kifor L, Study of the adrenal renin angiotensin system at a cellular level. Journal of Clinical Investigation 1995, September, in press.

What we claim is:

1. A method for treating erectile dysfunction in a subject, comprising:

administering to a subject in need of such treatment a therapeutically effective dose of a renin-angiotensin system inhibitor, to decrease the symptoms of erectile dysfunction, wherein the therapeutically effective dose is one which modifies acutely systemic blood pressure of the subject by less than 10%.

2. A method for treating erectile dysfunction as claimed in claim 1, wherein the renin-angiotensin system inhibitor is selected from the group consisting of an angiotensin II antagonist, an ACE inhibitor, or a renin inhibitor.

3. A method for treating erectile dysfunction as claimed in claim 2, wherein the renin-angiotensin system inhibitor is an angiotensin II antagonist.

4. A method for treating erectile dysfunction as claimed in claim 3, wherein the angiotensin II inhibitor is Losartan.

5. A method for treating erectile dysfunction as claimed in claim 2, wherein the renin-angiotensin system inhibitor is an ACE inhibitor.

6. A method for treating erectile dysfunction as claimed in claim 5, wherein the ACE inhibitor is selected from the group consisting of acylmercapto and mercaptoalkanoyl prolines, carboxyalkyl dipeptides, carboxyalkyl dipeptide mimics, and phosphinylalkanoyl prolines.

7. A method for treating erectile dysfunction as claimed in claim 5, wherein the ACE inhibitor is selected from the group consisting of enalapril and captopril.

8. A method for treating erectile dysfunction as claimed in claim 2, wherein the renin-angiotensin system inhibitor is a renin inhibitor.

9. A method for treating erectile dysfunction as claimed in claim 8, wherein the renin inhibitor is selected from the group consisting of a peptide, an amino acid, and an antibody to renin.

10. A method for treating erectile dysfunction as claimed in claim 2, wherein the therapeutic dose modifies acutely the systemic blood pressure of the subject by less than 5%.

11. A method for treating erectile dysfunction as claimed in claim 2, wherein the renin-angiotensin system inhibitor is administered by intracavernosal injection, intraurethral device, or penile patches.

12. A method for treating erectile dysfunction as claimed in claim 2, wherein the subject is otherwise free of indications calling for renin-angiotensin inhibition treatment.

13. A method for treating erectile dysfunction as claimed in claim 2, wherein the renin-angiotensin system inhibitor is administered orally.

14. A method for treating erectile dysfunction as claimed in claim 5, wherein the renin-angiotensin system inhibitor is administered orally.

15. A method for treating erectile dysfunction as claimed in claim 8, wherein the renin-angiotensin system inhibitor is administered orally.

16. A method for treating erectile dysfunction as claimed in claim 2 wherein the therapeutically effective dose is sufficient to increase intracavernosal pressure to a level substantially the same as the mean arterial pressure.

17. A method for improving erectile function in a subject free of symptoms of erectile dysfunction, comprising:

administering to a subject who is free of symptoms of erectile dysfunction a therapeutically effective dose of a renin-angiotensin system inhibitor, to improve erectile function.

18. A method for improving erectile function as claimed in claim 17, wherein the therapeutically effective dose is one that modifies the systemic blood pressure by less than 10%.

19. A method for improving erectile function as claimed in claim 17, wherein the inhibitor is selected from the group consisting of an angiotensin II inhibitor, an ACE inhibitor, and a renin inhibitor.

20. A method for improving erectile function as claimed in claim 19, wherein the renin-angiotensin system inhibitor is an angiotensin II antagonist.

21. A method for improving erectile function as claimed in claim 20, wherein the angiotensin II antagonist is Losartan.

22. A method for improving erectile function as claimed in claim 19, wherein the renin-angiotensin system inhibitor is administered orally.

* * * * *